(12) United States Patent
Xie et al.

(10) Patent No.: US 7,166,124 B2
(45) Date of Patent: Jan. 23, 2007

(54) METHOD FOR MANUFACTURING SUTURELESS BIOPROSTHETIC STENT

(75) Inventors: Hua Xie, Portland, OR (US); Lisa A. Buckley, New York, NY (US)

(73) Assignee: Providence Health System - Oregon, Seattle, WA (US)

( * ) Notice: Subject to any disclaimer, the term of this patent is extended or adjusted under 35 U.S.C. 154(b) by 0 days.

(21) Appl. No.: 10/104,391

(22) Filed: Mar. 21, 2002

(65) Prior Publication Data
US 2003/0181968 A1  Sep. 25, 2003

(51) Int. Cl.
*A61F 2/06* (2006.01)

(52) U.S. Cl. .................................... 623/1.13

(58) Field of Classification Search ............... 623/1.13, 623/1.14, 901
See application file for complete search history.

(56) References Cited

U.S. PATENT DOCUMENTS

| | | | |
|---|---|---|---|
| 5,556,414 A * | 9/1996 | Turi .......................... 623/1.11 |
| 5,569,239 A * | 10/1996 | Sinofsky ........................ 606/8 |
| 5,571,216 A | 11/1996 | Anderson |
| 5,693,085 A | 12/1997 | Buirge et al. |
| 5,697,969 A | 12/1997 | Schmitt et al. |
| 6,087,552 A | 7/2000 | Gregory |
| 6,187,039 B1 | 2/2001 | Hiles et al. |
| 6,206,931 B1 | 3/2001 | Cook et al. |
| 6,890,351 B2 * | 5/2005 | Termin et al. ............. 623/1.38 |
| 2001/0023370 A1 * | 9/2001 | Smith et al. ................ 623/1.13 |
| 2001/0039450 A1 | 11/2001 | Pavcnik et al. |

* cited by examiner

*Primary Examiner*—Michael Thaler
(74) *Attorney, Agent, or Firm*—Marger Johnson & McCollom, P.C.

(57) ABSTRACT

A bioprosthetic stent graft is disclosed, having a stent frame and a biomaterial sheath suturelessly bonded to the stent frame. Sutureless bonding avoids sutures and substantially reducing medical complications in implantation of the stent graft.

A device and method for manufacturing the stent graft further is disclosed. A mandrel is employed for shaping the stent graft, and means for irradiating the biomaterial effects sutureless bonding.

31 Claims, 4 Drawing Sheets

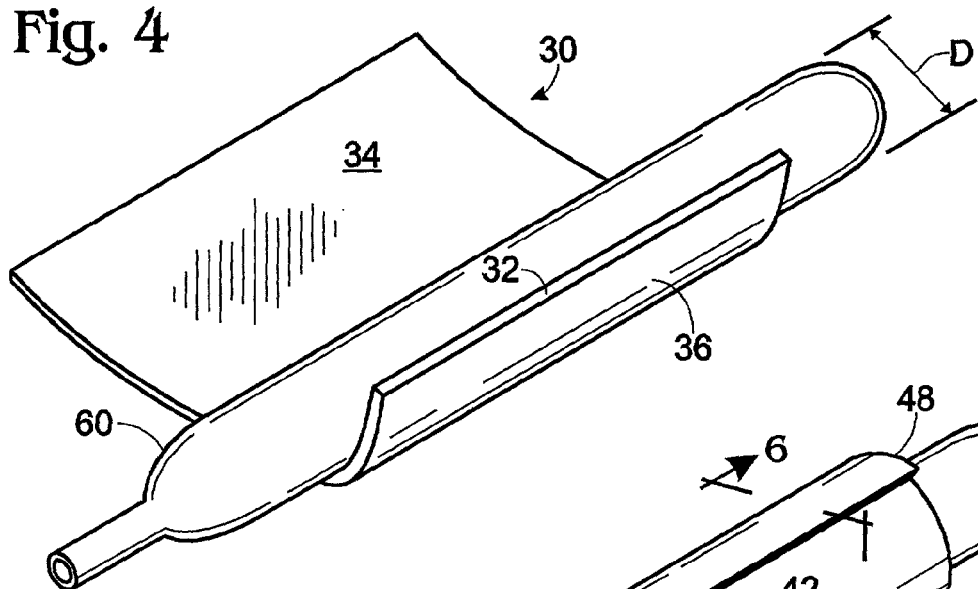
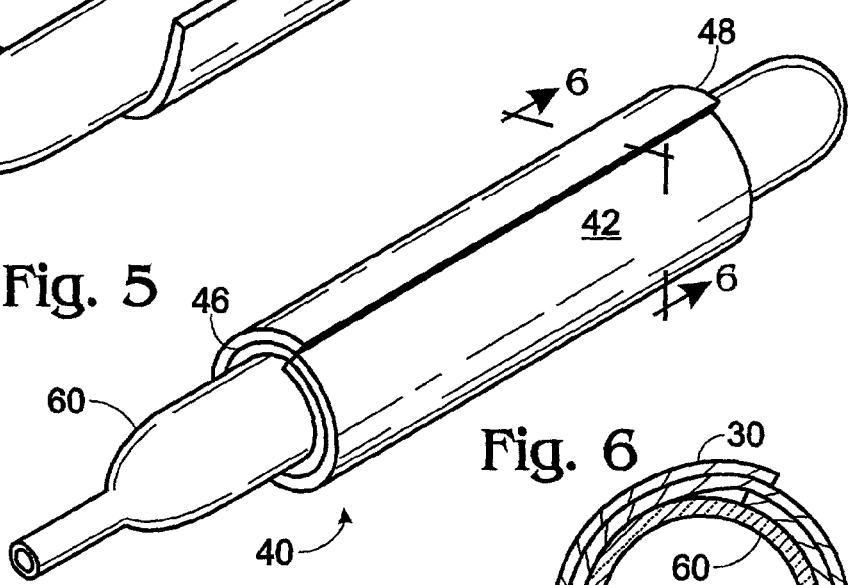
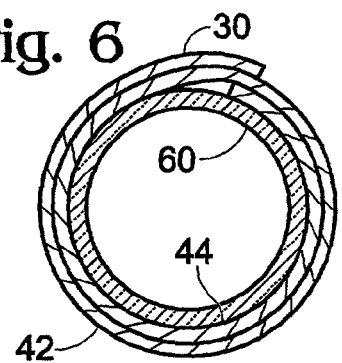
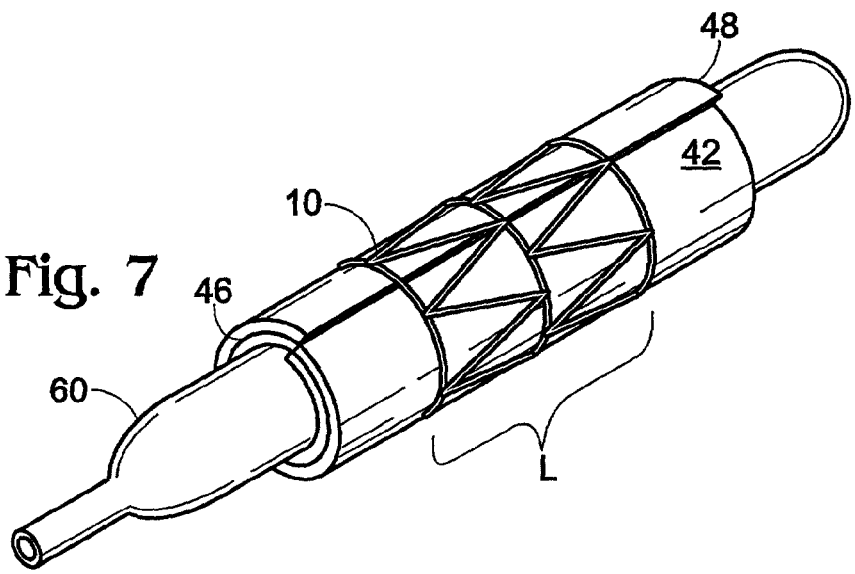

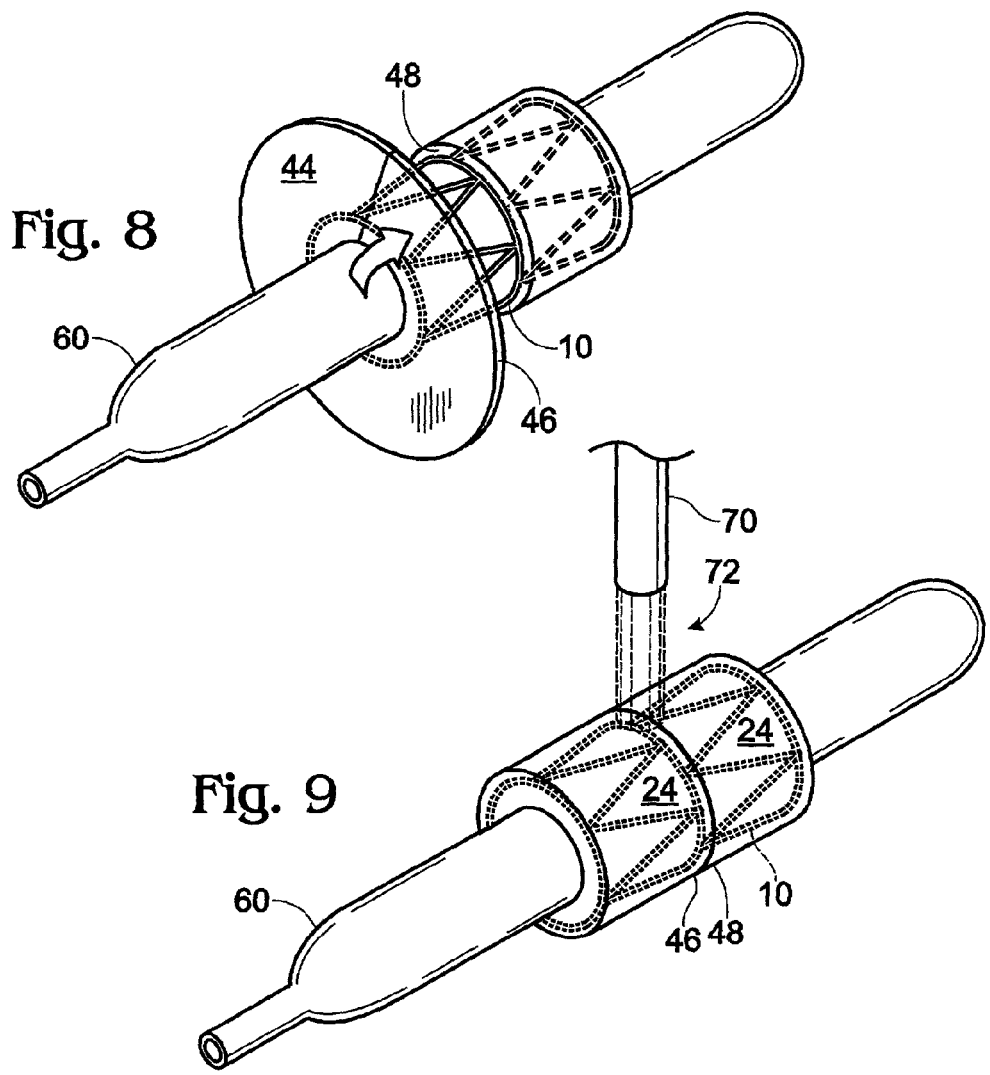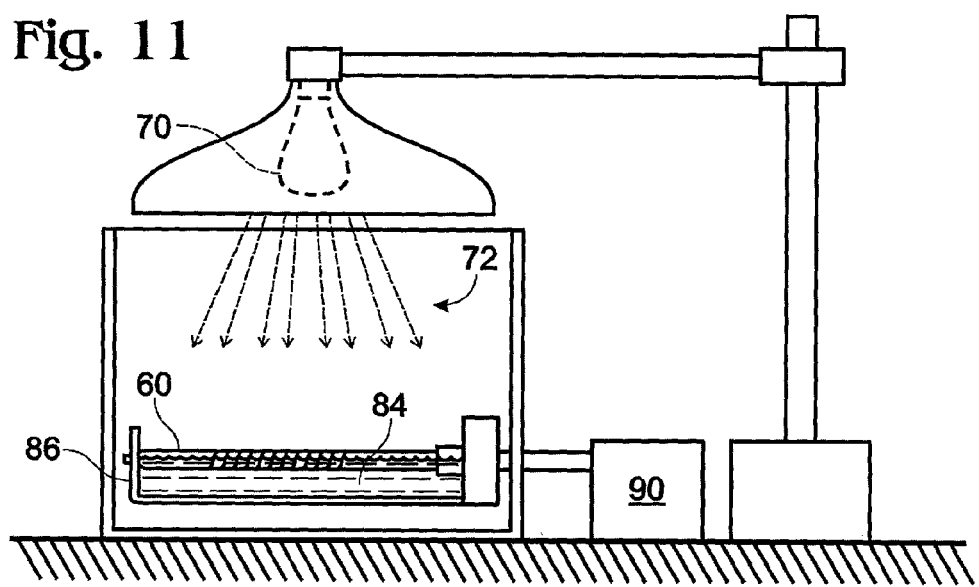

METHOD FOR MANUFACTURING SUTURELESS BIOPROSTHETIC STENT

This invention was made with the U.S. Government support under Grant Number DAMD17-96-1-6006, awarded by the Army Medical Research and Materiel Command. The U.S. Government may have certain rights in the invention.

BACKGROUND OF THE INVENTION

The present disclosure is related to the field of stents, and more specifically to an implantable, sutureless bioprosthetic stent graft comprising a biomaterial. The disclosure is further related to a device and a method for suturelessly bonding a biomaterial to a bioprosthetic frame of a stent graft.

Development of tissue substitutes has been undertaken for replacement and repair of damaged or diseased tissue and organs. Where there is a lack of native tissue, reconstruction generally is performed with an autograft, heterogaft and allograft. Various tissue grafts and synthetic biomaterials typically have been unsuccessful based on mechanical, structure, functional, or biocompatibility problems. There is therefore no ideal biomaterial for tissue replacement, particularly for soft tissue and tubular organs (e.g., vascular, trachea, esophagus, and biliary tract, and urinary tracts tissue).

Prosthetic stents and valves have been described in the prior art. Stents have been used with some success to overcome the problems of restenosis or re-narrowing of a vessel wall. Stents are exemplified by U.S. Pat. No. 6,293,968 (to Taheri) and U.S. Pat. No. 5,306,286 (to Stack et al.), which teaches a prosthetic stent constructed of synthetic materials. U.S. Pat. No 6,293,968 and U.S. Pat. No 5,306,286.

However, the use of such devices is often associated with thrombosis and other complications. Additionally, prosthetic devices implanted in vascular vessels can exacerbate underlying atherosclerosis.

Medical research therefore has focused on trying to incorporate artificial materials or biocompatible materials as bioprosthesis coverings to reduce the untoward effects of metallic device implantation, such as intimal hyperplasia, thrombosis and lack of native tissue incorporation.

Synthetic materials for stent coverings vary widely, e.g., materials such as Gore-Tex®, polytetrafluoroethylene (PTFE), and a resorbable yarn fabric (U.S. Pat. No. 5,697,969 to Schmitt et al.). Synthetic materials generally are not preferred substrates for cell growth.

Biomaterials and biocompatible materials also have been utilized in prostheses. Such attempts include a collagen-coated stent, taught in U.S. Pat. No. 6,187,039 (to Hiles et al.). As well, elastin has been identified as a candidate biomaterial for covering a stent (U.S. Pat. No. 5,990,379 (to Gregory)).

In contrast to synthetic materials, collagen-rich biomaterials are believed to enhance cell repopulation and therefore reduce the negative in vivo effects of metallic stents. It is believed that small intestinal submucosa (SIS) is particularly effective in this regard.

Some of the above-discussed coverings, while used to prevent untoward effects, actually exacerbate the effects to some extent. Accordingly, it is desirable to employ a native biomaterial or a biocompatible material to reduce post-procedural complications.

Mechanically hardier stent graft devices are required in certain implantation sites, such as cardiovascular, aortic, or other locations. In order to produce a sturdier bioprosthetic stent, a plurality of layers of biomaterial typically are used. Suturing is a poor technique for joining multiple layers of biomaterial. While suturing is adequate to join the biomaterial sheets to the metallic frame, the frame-sutured multiple sheets are not joined on their major surfaces and are therefore subject to leakage between the layers. Suturing of the major surfaces of the biomaterial layers also introduces holes into the major surfaces, increasing the risk of conduit fluid leaking through or a tear forming in one of the surfaces.

Heretofore, biomaterials have been attached to bioprosthetic frames using conventional suturing techniques. However, this approach is disadvantageous from manufacturing and implantation perspectives.

Suturing is time-consuming and labor-intensive. For example, suturing a sheet of biomaterial over a stent frame typically is a one- to two-hour process for a trained person and of the covered stents made, many are rejected. It is also an operator dependent process that can lead to issues with product uniformity and reliability. As well, suturing entails repeatedly piercing the biomaterial, creating numerous tiny punctures that can weaken the biomaterial and potentially lead to leakage and infection after the graft device has been installed.

Moreover, the presence of suture material can enhance the foreign body response and lead to tubular vessel narrowing at the implantation site.

As an alternative to suturing, U.S. Pat. Nos. 5,147,514, 5,332,475, and U.S. Pat. No 5,854,397 describe processes for photo-oxidizing collageneous material in the presence of a photo-catalyst to crosslink and stabilize the collageneous material. Reconstituted soluble collagen fibrils are taught to be mixed and suspended in solutions containing a photo-catalyst, so that a photo-oxidizative cross-linking process can be performed to produce stabilized collagen products.

However, the references fail to teach crosslinking of collagen fibrils between two individual native tissues, as well as fusion of those separate tissue pieces using photo-oxidization techniques.

Biocompatible adhesive compounds also have been investigated as alternatives to suturing. For example, fibrin glue, a fibrinogen polymer polymerized with thrombin, has been used as a tissue sealant and hemostatic agent.

Bioadhesives generally produce rigid, inflexible bond regions that can lead to local biomaterial tears and failure of the graft device. In addition, some bioadhesives and photo-chemical cross-linking agents (e.g., glutaraldehyde) carry risk of acute and chronic toxicity and biocompatibility.

Bio-tissue welding, using a laser, is known in the art, e.g., U.S. Pat. No. 5,156,613 (to Sawyer). This technique uses light energy to heat an area of tissue sufficiently to denature at least a portion of the tissue constituents and fuse them together.

BRIEF DESCRIPTION OF DRAWINGS

FIGS. 4–9 are diagrams of a method for constructing a sutureless bioprosthetic stent graft according to the present disclosure.

FIGS. 10–11 are side view diagrams of two embodiments of a device for manufacturing a sutureless bioprosthetic stent graft according to the disclosed method.

DETAILED DESCRIPTION OF EMBODIMENTS

Figure 1:
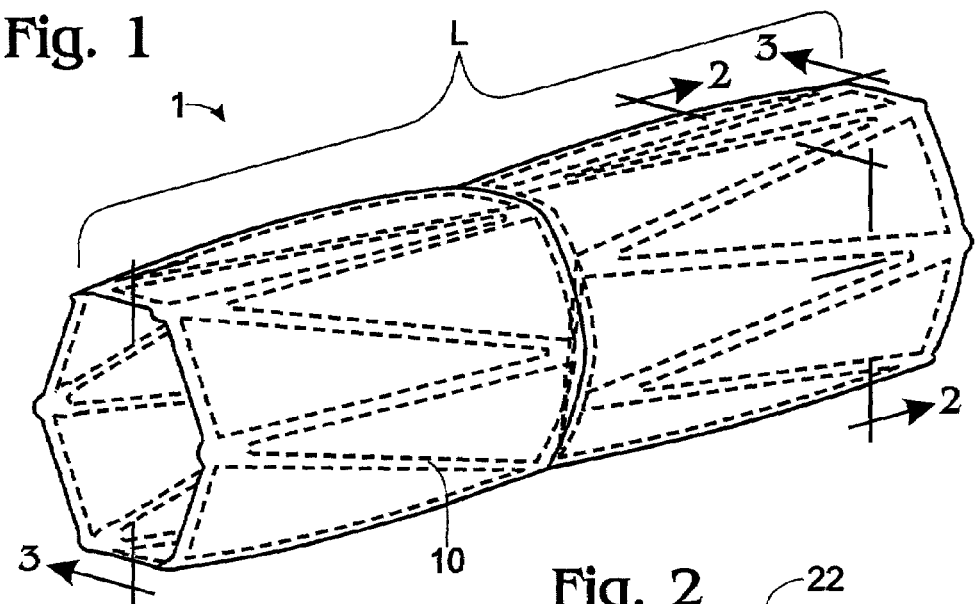
FIG. 1 is a perspective view of a sutureless bioprosthetic stent graft constructed according to the method disclosed herein.
Figure 2:
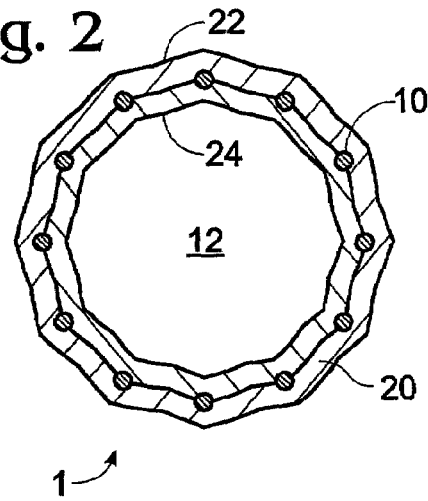
FIGS. 2–3 are lateral and longitudinal cross-sectional views, respectively, of the valve graft of FIG. 1.
Figure 3:
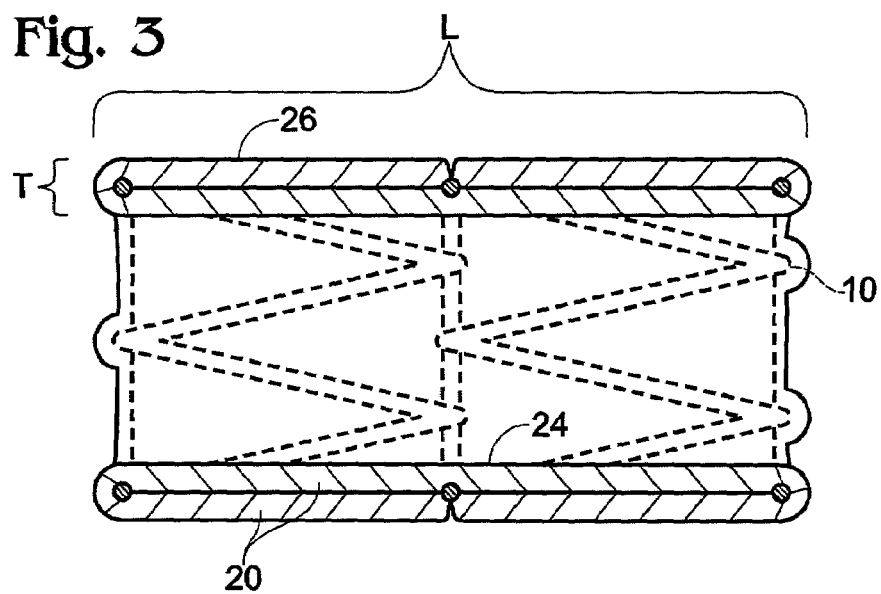

A sutureless bioprosthetic stent graft according to the present disclosure is shown in FIGS. 1–3. The stent graft 1 comprises a typically cylindrical stent frame 10 having a length L and defining a lumen 12. The stent graft further has a sheath of biomaterial 20 suturelessly attached to and substantially covering the stent frame.

The stent frame 10 preferably is constructed of a fine-gauge metal (e.g., 0.014 inch diameter) of a flexible character. Such frame enables the stent graft to be expanded or compressed in diameter or length.

A stent frame of this type can be made of a shape memory material. Such a shape memory wire frame is known in the art as a frame that substantially returns to its original shape after it is deformed and then released, as described in U.S. Pat. No. 4,512,338 (to Balko et al.).

Other materials can be effectively employed as the substrate for a stent frame, for example, a synthetic material such as TEFLON (polytetrafluoroethylene), DACRON or a biodegradable composition. Alternative compositions can in some cases be of a memory character.

The stent frame is covered with a biomaterial sheath 20 having a selected thickness T. The biomaterial sheath can comprise a single layer, a single layer with a partial overlap, or a plurality of layers (single or multiple sheets) coupled to the supporting stent frame. The sheath of biomaterial preferably comprises both the inner stent graft surface 24 and the outer stent graft surface 26.

If the biomaterial sheath is constructed of a plurality of layers of biomaterial, the plurality of layers of biomaterial can be positioned on the inner stent graft surface 24, the outer stent graft surface 26, or both inner and outer stent graft surfaces.

The biomaterial can be comprised of a natural or synthetic compound, and preferably is a collagen-rich material. Suitable natural biomaterials include collagen, small intestine submucosa, pericardial tissue, and elastin. Combinations of the above biomaterials also can be envisioned.

Alternatively, the biomaterial can be synthetic, for example, TEFLON or DACRON coated with albumin or a collagen-containing substrate.

The biomaterial formed into a sheath is bonded to the stent frame without the use of conventional sutures. Avoidance of suture material mitigates the risk of a foreign body response by the host patient, a response that can lead to a narrowing of the tubular vessel in which the graft is implanted.

Such stent grafts might be used, for example, in the cardiovascular system (e.g., in an artery or vein), the gastrointestinal tract, the urinary tract, or the trachea. The stent graft as disclosed permits fluid flow direction through the conduit while preventing leakage out of the conduit.

Implantation of a stent graft according to the present disclosure provides several benefits over prior art stents. Collagen and SIS are known to provide a matrix that encourages native cell repopulation and may ultimately enhance tissue repair and regeneration as well as integration of implanted supporting structure materials.

A method for making a first embodiment of a bioprosthetic stent graft generally comprises wrapping a collagen-rich biomaterial on a mandrel to form a multi-layer structure thereon, and suturelessly bonding together the multiple layers of the biomaterial. The method can be employed to produce a stent graft composed of a biomaterial and further comprising a synthetic stent frame.

In one embodiment of the method, a sheet of biomaterial 30 is provided, having a first edge 32, an inward-facing surface 34 and an outward-facing surface 36.

As stated above, the biomaterial sheet can be comprised of a natural or synthetic compound, and preferably is a collagen-rich material. The use of a reconstructed small intestine submucosa (SIS) is especially advantageous. Reconstructed SIS biomaterial can be obtained in accordance with the description in the prior U.S. Pat. Nos. 4,956,178 and 4,902,508.

The biomaterial can have incorporated therein a drug or other bioactive compound. The incorporation of such compounds allows for the most efficacious delivery of the drug to the implantation site.

The biomaterial sheet 30 is wrapped on a mandrel 60 to form a biomaterial roll 40. As shown in FIGS. 4–5, wrapping can be performed by approximating the first edge 32 of the biomaterial sheet 30 longitudinally along the mandrel 60, then rotating the mandrel. Of course, it is also possible to immobilize the mandrel and wrap the biomaterial sheet around it.

As formed and shown in FIGS. 5–6, the biomaterial roll 40 has a first major surface 42, a second major surface 44, a first end 46, and a second end 48.

A stent frame 10 then is positioned over the first major surface 42 of the biomaterial roll 40 and intermediate the first and second ends 46,48 of the biomaterial roll (FIG. 7).

The stent frame is shown being encased with the biomaterial in FIG. 8. At least the first end 46 of the biomaterial roll 40 is everted back over the stent frame 10, covering and embedding it within the biomaterial roll. The first end 46 can be approximated to the first major surface 42 of the biomaterial roll proximate the second end 48.

In a first alternative embodiment shown in FIG. 8, the first end 46 and the second end 48 both can be everted and folded back over the stent frame to encase the frame in biomaterial. In this embodiment, the first end and the second end of the biomaterial roll can be approximated to one another.

In a second alternative embodiment, a second sheet of biomaterial can be laid over the stent frame to cover it and abut the second biomaterial sheet with the first major surface of the biomaterial roll.

The biomaterial, i.e., the approximated first end and the biomaterial roll to which it is abutted, is suturelessly bonded by irradiating with energy 72. In the embodiments wherein one or both ends of the biomaterial roll were everted, suturelessly bonding comprises suturelessly bonding the first and second ends of the biomaterial to one another or to the first major surface 42 of the biomaterial roll 40.

Sutureless bonding can be accomplished using any one of a variety of mechanisms. In a preferred embodiment, sutureless bonding is via thermal fusion. The biomaterial roll is irradiated with energy 72 sufficient to at least partially thermally fuse the biomaterial sheet.

Sutureless bonding using thermal fusion preferably is carried out with a laser, most preferably emitting light having a wavelength of about 800 nm. Alternative means for suturelessly bonding the biomaterial using thermal fusion techniques are known in the art. Devices producing appropriate energy include a radio-frequency energy source, an ultrasound energy source, and contact electro-thermal transducer.

To facilitate thermal fusion and localize the thermal energy to the site of sutureless bonding, an energy-absorbing material can be utilized. For use with a laser, the energy-absorbing material typically is energy-absorptive within a predetermined range of light wavelengths. An energy-absorbing material suitable for use with an 800 nm laser is indocyanine green.

Sutureless bonding using an 800 nm laser can also be performed by laser welding, using tissue welding solder or patches. Tissue welding solder, known in the art, typically is a viscous proteinaceous fluid, such as an albumin solution. Welding patches can be dried strips of albumin, collagen, elastin, or similar compounds. The solder or welding patch can have incorporated therein an energy-absorbing material.

In place of thermal fusion, photo-chemical cross-linking alternatively can be employed to suturelessly bond the biomaterial. In general, a crosslinking agent is used, and cross-linking is accomplished by reacting the crosslinking agent to form attachments to the abutted pieces of biomaterial (e.g., the first and second ends, as described above).

A representative photo-chemical crosslinking step comprises treating the biomaterial with methylene blue, then irradiating the biomaterial roll with visible or ultraviolet light.

Sutureless bonding can be spatially limited to the abutted ends 46,48 of the biomaterial roll, but can also include irradiating selected loci on, or the entirety of, the first major surface 42, the second major surface 44, or both the first and second major surfaces 42,44 of the biomaterial roll 40.

Irradiating a plurality of loci on the biomaterial roll with energy can be facilitated by rotating the mandrel 60 during irradiating.

The biomaterial preferably is substantially dehydrated prior to suturelessly bonding. This alternative step makes the biomaterial more self-adhesive (that is, "stickier"), which aids in retaining the biomaterial surface and edges in an approximated orientation. Further, dehydration enhances the optical transmission into the biomaterial, improving light-mediated sutureless bonding.

Substantial dehydration of the biomaterial is especially advantageous when sutureless bonding is via photo-crosslinking. For laser-mediated sutureless bonding, the biomaterial need not be substantially dehydrated, although removal of some fluid from the biomaterial is preferable.

In the above alternative method, rehydration typically proceeds contemporaneous with irradiating, that is, during and/or after sutureless bonding by irradiation of the biomaterial roll.

The suturelessly bonded biomaterial roll and encased stent frame then are removed from the mandrel. Removal generally is accomplished by sliding the stent graft 1 off the end of the mandrel 60. Alternatively, the mandrel can be of an expandable or balloon-type construction, and can be deflated to assist in stent graft removal.

A device is disclosed for manufacturing a sutureless bioprosthetic stent graft. The device generally comprises a mandrel 60 and an energy-irradiating means 70. In an alternative embodiment discussed below, the energy-irradiating means 70 and the mandrel 60 can be structurally combined.

In one embodiment as shown in FIGS. 4–5 and 7–9, the mandrel 60 preferably is a roughly cylindrical structure having a selected diameter D, adapted to have positioned on it a stent graft comprising a biomaterial sheath. The stent graft 1 fabricated thereon, described more fully above, typically has a shape matching the shape of the mandrel 60 and will have a lumen corresponding to the diameter D of the mandrel.

The diameter and shape of the mandrel can be customized to produce a sutureless stent graft having a desired lumen configuration. For example, the mandrel can have a constant diameter corresponding to the inner diameter of a cylindrical stent graft fabricated thereon.

Alternatively, the mandrel can be tapered, permitting formation thereon of a tapering sutureless stent graft. In yet another alternative embodiment, the mandrel can have an increased or decreased central diameter, adapted to produce a stent graft with a central portion that is outwardly- or inwardly-bulging.

The mandrel can be constructed of a variety of materials, such as metal, plastic, or other rigid material. The mandrel preferably is constructed of a material that is non-reactive to the energy outputted by the energy-irradiating means.

Wire or a flexible compound can be employed in the manufacture of a first alternative embodiment of the mandrel. A wire mandrel can have a cage-like or coiled structure, providing sufficient structure for a biomaterial roll to be formed thereon.

In a second alternative embodiment, a balloon-type mandrel can be utilized, as shown in FIGS. 7–9. A balloon-type mandrel can be inflated to a selected diameter and a stent graft manufactured thereon, after which the mandrel is deflated to remove the stent graft.

Figure 10:
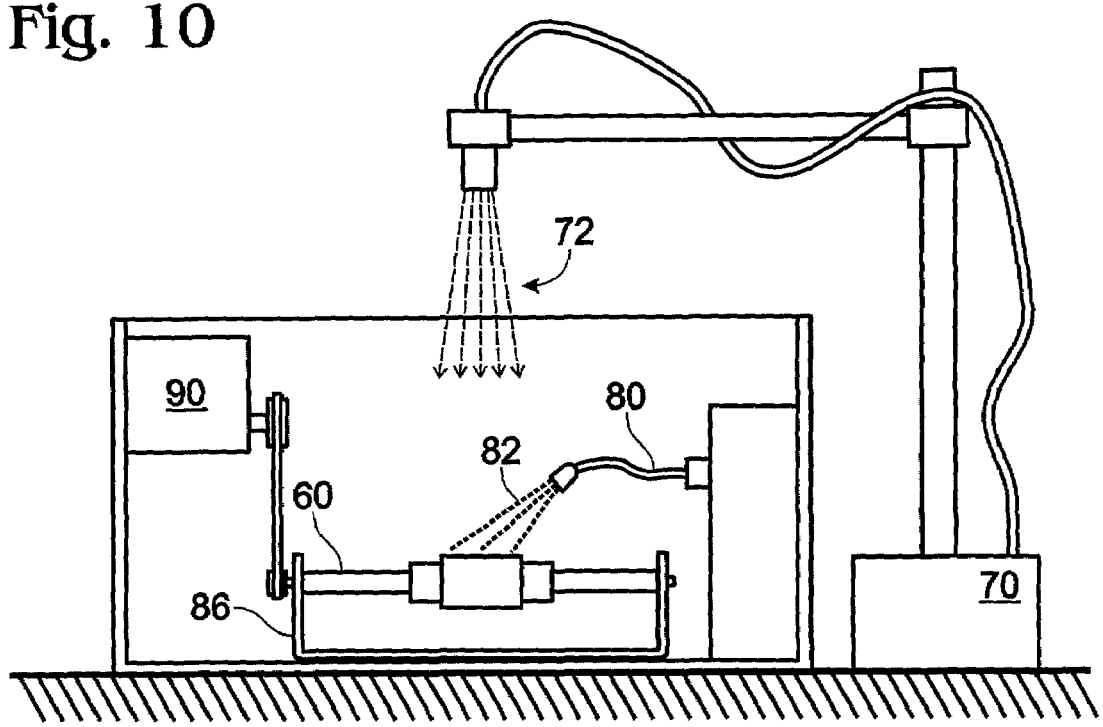

The energy-irradiating means 70 is adapted to irradiate a biomaterial sheath with energy 72 when the biomaterial sheath is positioned on the mandrel 60. Irradiation results in suturelessly bonding via either a thermal bonding or photo-chemical crosslinking mechanism. In the embodiments of FIGS. 10–11, means for irradiating is configured to irradiate the first major surface 42 of a biomaterial roll 40 positioned on the mandrel 60.

Means for irradiating the biomaterial sheath with energy can be a light source, such as a white light source, or an ultraviolet source. Such light sources are especially suitable for photo-chemical crosslinking, using a photo-active crosslinking agent such as methylene blue.

In an embodiment using light energy, a laser can be employed, preferably operative to emit light having a wavelength of about 800 nm. The laser is positioned to irradiate a biomaterial roll on the mandrel.

In other alternative embodiments, the energy-irradiating means can be an ultrasound energy source, a radio-frequency energy source, or a contact electro-thermal transducer.

Figure 12:
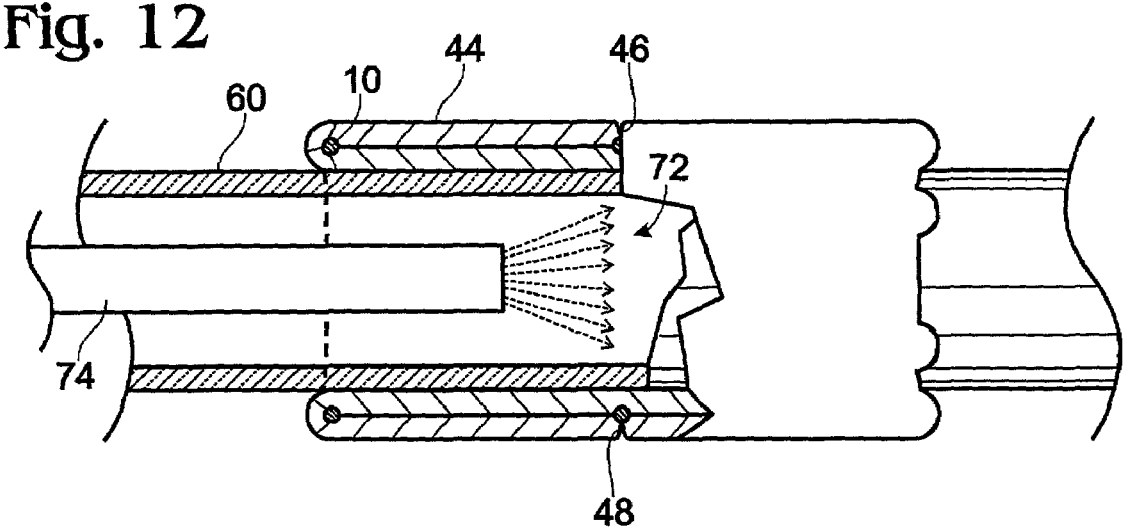
FIG. 12 is a cutaway perspective diagram of a mandrel of the present device, having housed therein means for irradiating with energy.

In yet another alternative embodiment, means for irradiating 70 can be configured inside the mandrel 60 (FIG. 12). This configuration permits irradiation of the second major surface 44 of a biomaterial roll 40 positioned on the mandrel 60. An irradiating means inside the mandrel can be employed as an alternative to, or in addition to, an external irradiating means to permit irradiation of the second major surface or both the first and second major surfaces, respectively, of a biomaterial roll. The fiber-optic element 72 is housed at least partially within the mandrel 60. The fiber-optic element is adapted to transmit light from a light source 70 to the mandrel, to irradiate the second major (or inward-facing) surface 44 of a biomaterial sheath positioned on the mandrel. Irradiating with energy can be undertaken by emitting light energy from the fiber tip positioned at one end of the biomaterial roll, and then advancing or retracting the fiber to reposition the fiber tip adjacent the desired locus for sutureless bonding thereat.

The device can further include means for moistening 80 a biomaterial sheath when said sheath is positioned on the mandrel. Moistening can be accomplished via an injecting or misting element 82 adapted to emit a mist of fluid or other appropriate moistening matter.

Alternatively, fluid 84 can be maintained in a well 86, with the mandrel positioned above said fluid. So oriented, the lower-most portion of the biomaterial roll 40 on the mandrel will contact the fluid and be wetted thereby.

In the embodiment wherein dehydrating and rehydrating of the biomaterial roll is performed, moistening means 80 can be used to rehydrate the biomaterial roll 40. Rehydration can be accomplished by, for example, misting fluid onto the biomaterial roll, by controlling the level of the fluid so as to selectively contact the biomaterial roll with the fluid, or by raising and lowering the mandrel to bring the roll into or out of contact with the fluid.

Rotating means 90 for rotating the mandrel 60 further can be utilized to rotate a stent graft positioned on the mandrel. Rotating enables the entire outward-facing (first major) surface 42 of the biomaterial sheath to be accessible to the moistening means 80.

Rotation of the mandrel further permits the energy-irradiating means 70 to be directed to varying areas of the outward-facing surface of the biomaterial sheath. Rotating, whether continuous or coordinated with irradiating, is advantageous for irradiating specific loci on the outward-facing surface.

A person skilled in the art will be able to practice the present invention in view of the description present in this document, which is to be taken as a whole. Numerous details have been set forth in order to provide a more thorough understanding of the invention. In other instances, well-known features have not been described in detail in order not to obscure unnecessarily the invention.

While the invention has been disclosed in its preferred form, the specific embodiments presented herein are not to be considered in a limiting sense. Indeed, it should be readily apparent to those skilled in the art in view of the present description that the invention can be modified in numerous ways. The inventor regards the subject matter of the invention to include all combinations and sub-combinations of the various elements, features, functions and/or properties disclosed herein.

What is claimed is:

1. A method for manufacturing a sutureless bioprosthetic stent graft suitable for physiological implantation, comprising:
   wrapping a sheet of biomaterial on a mandrel to form a biomaterial roll having a first end, a second end, a lumen-facing first surface, an outward-facing second surface and an at least partial overlap of the biomaterial, the biomaterial first and second surfaces consisting essentially of an optically-transmissive collagen-rich matrix suitable for cell repopulation;
   positioning a stent frame over the second surface of the biomaterial roll and intermediate the first and second ends of the biomaterial roll;
   everting the first end of the biomaterial roll over the stent frame to encase the stent frame within apposed second surfaces of the biomaterial;
   suturelessly bonding the biomaterial; and
   removing the biomaterial roll from the mandrel;
   wherein suturelessly bonding the biomaterial consists of photo-chemically cross-linking the collagen-rich matrix of the apposed second surfaces of the biomaterial by applying a photo-active crosslinking agent to the second surface to provide a photo-activable light absorptive surface on the optically-transmissive collagen rich matrix and irradiating at least the first end of the biomaterial roll with visible or UV light.

2. The method of claims 1, wherein wrapping comprises aligning a first edge of the biomaterial sheet along the mandrel and rolling said mandrel.

3. The method of claim 1, wherein everting the first end of the biomaterial roll over the stent frame comprises everting the first end of the biomaterial roll over the stent frame to approximate said first end with the second end.

4. The method of claim 1, wherein the crosslinking agent is methylene blue.

5. The method of claim 4, wherein irradiating the biomaterial roll with energy comprises irradiating the biomaterial roll with visible light.

6. The method of claim 4, wherein irradiating the biomaterial roll with energy comprises irradiating the biomaterial roll with ultraviolet light.

7. The method of claim 1, further comprising rotating the covered stent during irradiating.

8. The method of claim 1, further comprising dehydrating the biomaterial prior to suturelessly bonding; and rehydrating the biomaterial contemporaneous with suturelessly bonding.

9. The method of claim 1, wherein irradiating the biomaterial roll comprises irradiating substantially the entire second surface of the biomaterial roll.

10. The method of claim 1, wherein irradiating the biomaterial roll comprises irradiating substantially the entire lumen-facing first surface of the biomaterial roll.

11. The method of claim 1, wherein the biomaterial sheet consists essentially of collagen.

12. The method of claim 1, wherein the biomaterial consists essentially of small intestine submucosa.

13. The method of claim 1, wherein the biomaterial has incorporated therein a drug.

14. A method for manufacturing a sutureless bioprosthetic stent graft suitable for physiological implantation, comprising:
   wrapping a sheet of biomaterial on a mandrel to form a biomaterial roll having a first end, a second end, a lumen-facing first surface, an outward-facing second surface and an at least partial overlap of the biomaterial, the biomaterial first and second surfaces consisting essentially of an optically-transmissive collagen-rich matrix suitable for cell repopulation;
   positioning a stent frame over the second surface of the biomaterial roll and intermediate the first and second ends of the biomaterial roll;
   everting the first end of the biomaterial roll over the stent frame to encase the stent frame within apposed second surfaces of the biomaterial;
   applying to the second surface an energy absorbing material to provide a photo-activable wavelength-selective surface on the collagen-rich matrix that is energy-absorptive within a predetermined range of visible light wavelength and consists of an energy absorbing dye;
   suturelessly bonding the biomaterial by irradiating at least the first end of the biomaterial roll with energy visible light of a wavelength within the predetermined range; and
   removing the biomaterial roll from the mandrel, wherein suturelessly bonding the biomaterial consists of irradiating the biomaterial roll sufficiently with light of said wavelength generated by a laser to at least partially thermally fuse the collagen rich matrix of the apposed second surfaces of the biomaterial sheet together.

15. The method of claim 14, wherein the energy-absorbing dye is indocyanine green.

16. The method of claim 15, wherein irradiating the biomaterial roll with energy generated by a laser includes irradiating the biomaterial roll with energy generated by a laser generating light having a wavelength of about 800 nm.

17. The method of claim 14, further comprising applying an energy absorbing material that is energy absorptive within a predetermined range of light wavelengths and consists of an energy absorbing dye,
    wherein suturelessly bonding the biomaterial includes suturelessly bonding selected loci on the biomaterial roll,
    wherein the biomaterial consists essentially of small intestine submucosa,
    and wherein suturelessly bonding selected loci on the biomaterial roll comprises irradiating the biomaterial roll at selected loci with light generated by a laser, said light being sufficient to at least partially thermally fuse the biomaterial sheet at the selected loci.

18. The method of claim 17 wherein the energy-absorbing dye is indocyanine green.

19. The method of claim 18 wherein irradiating the biomaterial roll at selected loci with energy generated by a laser includes irradiating the biomaterial roll at selected loci with energy generated by a laser emitting light having a wavelength of about 800 nm.

20. The method of claim 14 further comprising:
    dehydrating the biomaterial prior to suturelessly bonding;
    wherein suturelessly bonding the biomaterial roll includes contemporaneous rehydration of the biomaterial.

21. The method of claim 14, wherein the biomaterial has incorporated therein a drug.

22. A method for manufacturing a sutureless bioprosthetic stent graft suitable for physiological implantation, comprising:
    forming a biomaterial sheet into a biomaterial roll on a mandrel, said biomaterial roll having a first end, a second end, an inward-facing first surface, an outward-facing second surface and an at least partial overlap of the biomaterial, the biomaterial consisting essentially of small intestine submucosa;
    positioning a stent frame over the biomaterial roll and intermediate the first and second ends thereof;
    everting the first end of the biomaterial roll over the stent frame;
    encasing the stent frame within the biomaterial sheet;
    at least partially suturelessly bonding apposed second surfaces of the biomaterial roll; and
    removing the biomaterial roll from the mandrel,
    wherein suturelessly bonding the biomaterial roll consists of photo-chemically cross-linking the apposed second surfaces of the biomaterial by applying a photo-active crosslinking agent to the second surface and irradiating at least the first end of the biomaterial roll with visible or UV light.

23. The method of claim 22 wherein the crosslinking agent is methylene blue.

24. The method of claim 23 wherein irradiating the biomaterial roll with energy comprises irradiating the biomaterial roll with visible light.

25. The method of claim 23 wherein irradiating the biomaterial roll with energy comprises irradiating the biomaterial roll with ultraviolet light.

26. The method of claim 22, further comprising rotating the covered stent during irradiating.

27. A method for manufacturing a sutureless bioprosthetic stent graft suitable for physiological implantation, comprising:
    forming a biomaterial sheet into a biomaterial roll on a mandrel, said biomaterial roll having a first end, a second end, an inward-facing first surface, an outward-facing second surface and an at least partial overlap of the biomaterial, the biomaterial consisting essentially of small intestine submucosa;
    positioning a stent frame over the biomaterial roll and intermediate the first and second ends thereof;
    evening the first end of the biomaterial roll over the stent frame;
    encasing the stent frame within the biomaterial sheet;
    applying to the second surface of the biomaterial an energy absorbing material that is energy-absorptive within a predetermined range of visible light wavelengths consisting of an energy absorbing dye;
    at least partially suturelessly bonding apposed second surfaces of the biomaterial roll; and
    removing the biomaterial roll from the mandrel,
    wherein suturelessly bonding the biomaterial roll consists of irradiating the biomaterial roll sufficiently with visible light of said wavelength generated by a laser to at least partially thermally fuse the apposed second surfaces of the biomaterial sheet together.

28. The method of claim 27 wherein the energy-absorbing dye is indocyanine green.

29. The method of claim 28 wherein irradiating the biomaterial roll with energy sufficient to at least partially thermally fuse the biomaterial sheet with energy generated by a laser includes irradiating the biomaterial roll with energy sufficient to at least partially thermally fuse the biomaterial sheet with energy generated by a laser emitting light having a wavelength of about 800 nm.

30. The method of claim 27 wherein suturelessly bonding the biomaterial roll comprises suturelessly bonding selected loci on the apposed second surfaces of the biomaterial roll.

31. The method of claim 27 wherein suturelessly bonding the biomaterial roll comprises suturelessly bonding selected loci on the biomaterial roll by irradiating the biomaterial roll at selected loci with energy generated by a laser, said energy being sufficient to at least partially thermally fuse the biomaterial sheet.

* * * * *

UNITED STATES PATENT AND TRADEMARK OFFICE
CERTIFICATE OF CORRECTION

PATENT NO.        : 7,166,124 B2
APPLICATION NO.   : 10/104391
DATED             : January 23, 2007
INVENTOR(S)       : Xie et al.

It is certified that error appears in the above-identified patent and that said Letters Patent is hereby corrected as shown below:

Column 8, line 64, "roll with energy visible light" should read --roll with visible light--.

Column 10, line 24, "evening the first end" should read --everting the first end--.

Signed and Sealed this

Eighteenth Day of December, 2007

JON W. DUDAS
*Director of the United States Patent and Trademark Office*